United States Patent [19]

Dazord et al.

[11] 4,158,673

[45] Jun. 19, 1979

[54] PROCESS FOR THE SYNTHESIS OF BIS(ALKYL SULPHIDE)-DECABORANE (12)

[75] Inventors: Jacques L. Dazord; Henri M. Mongeot, both of Villeurbanne; Gildas J. Guillevic, Avon, all of France; Jean F. Cueilleron, deceased, late of Lyons, France, by Pierre M. Bouvier, Executor

[73] Assignee: Etat Francais, France

[21] Appl. No.: 840,627

[22] Filed: Oct. 11, 1977

[30] Foreign Application Priority Data

Oct. 11, 1976 [FR] France .............................. 76 30420

[51] Int. Cl.² ............................................... C07F 5/02
[52] U.S. Cl. ............................................... 260/606.5 B
[58] Field of Search .................................. 260/606.5 B

[56] References Cited

U.S. PATENT DOCUMENTS

| 3,154,561 | 10/1964 | Muetterties | 260/606.5 B X |
| 3,296,260 | 1/1967 | Knoth | 260/606.5 B X |
| 3,489,812 | 1/1970 | Marshall et al. | 260/606.5 B |

*Primary Examiner*—Helen M. S. Sneed
*Attorney, Agent, or Firm*—Bucknam and Archer

[57] ABSTRACT

The invention relates to a process for the synthesis of bis(alkyl sulphide)-decaboranes (12).

This synthesis is characterized in that a decahydrodecaborate (2−) salt of the general formula $M_2B_{10}H_{10}$, in which M represents a positive radical, is treated with a mixture comprising a strong oxygen-containing acid and an alkyl sulphide of the formula $R_2S$, in which R is a lower alkyl radical. In a preferred procedure, the said mixture is a solution of a strong oxygen-containing acid which is saturated with an alkyl sulphide.

The bis(alkyl sulphide)-decaboranes (12) are especially useful in the synthesis of certain carboranes.

9 Claims, 1 Drawing Figure

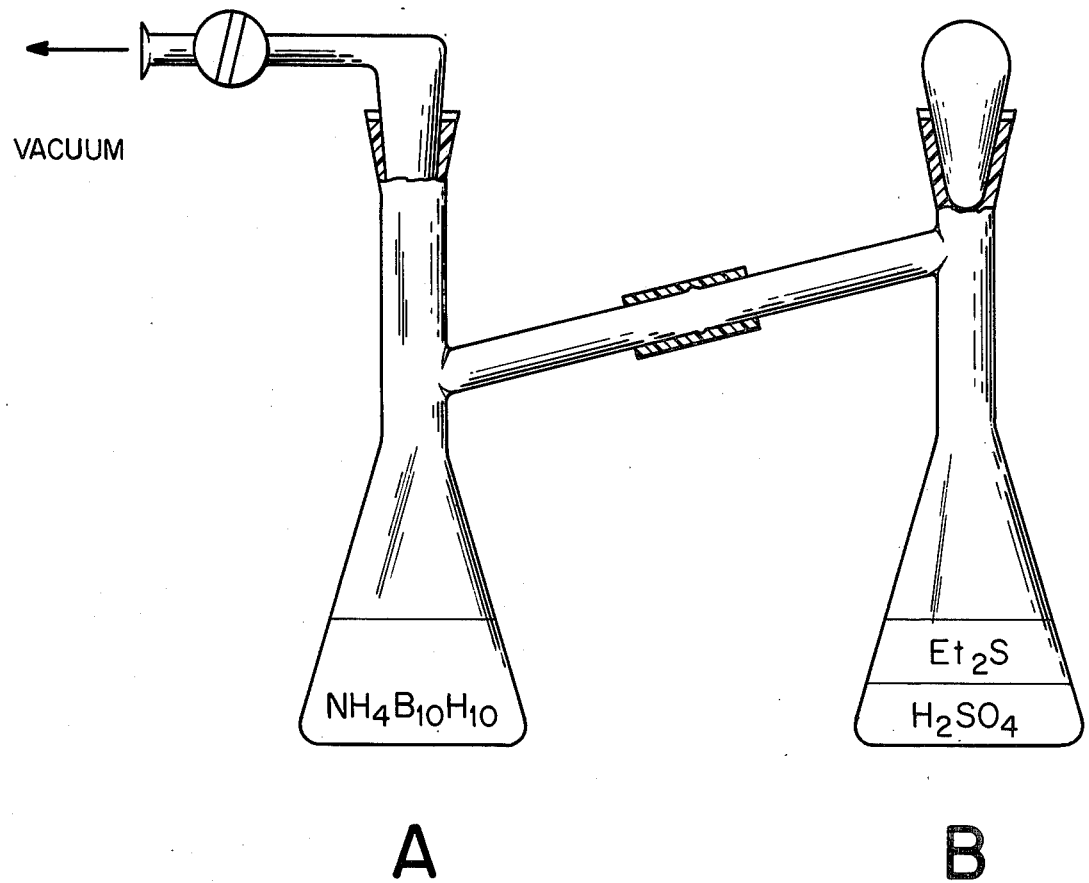

PROCESS FOR THE SYNTHESIS OF BIS(ALKYL SULPHIDE)-DECABORANE (12)

The present invention relates to a process for the synthesis of bis(alkyl sulphide)-decaboranes (12), which are intermediates in the synthesis of certain carboranes.

The carboranes are well known and certain of them are involved especially in the manufacture of thermostable plastics, for example of copolymers. These polymers possess very good mechanical properties which are preserved at temperatures of over 600° C. By way of indication, there may be mentioned the tensile strength, which is of the order of 50 kg/cm$^2$, and the elongation, which reaches 200 to 300%.

According to a first process of preparation described in the review given in "J. Amer. Chem. Soc. 1957, 79," 1006–1007, a bis-ligand $B_{10}H_{12}L_2$ is prepared by the action of a Lewis base L on decaborane according to the following reaction:

$$B_{10}H_{14} + 2L \rightarrow B_{10}H_{12}L_2 + H_2 \qquad (1)$$

However, this reaction requires the use of decaborane which is an expensive and very toxic product.

According to a process described in U.S. Pat. No. 3,489,812, the synthesis of bis(ethyl sulphide)-decaborane is carried out by the conjoint action of gaseous hydrochloric acid and ethyl sulphide on ammonium decahydrodecaborate according to the reaction:

However, this synthesis requires the use of ammonium decahydrodecaborate of which the only process of preparation which can be used industrially employs tetraethylammonium decahydrodecaborate. The latter is itself prepared by the pyrolysis of tetraethylammonium borohydride $Et_4NBH_4$.

On the other hand, this process can only be used with gaseous hydrochloric acid, and it is necessary to carry out the reaction in a non-oxidising medium, for example in the presence of an inert gas.

Finally, the yield of the reaction, calculated on the initial amount of $(NH_4)_2B_{10}H_{10}$, is fairly low and is of the order of 30%.

The present invention makes it possible to avoid the abovementioned disadvantages by providing a process of preparation of bis(alkyl sulphide)-decaborane which can advantageously be used directly, on the one hand, on $(Et_4N)_2B_{10}H_{10}$, which is a product of the pyrolysis of $Et_4NBH_4$, and, on the other hand, on other decahydrodecaborate (2−) salts (including ammonium decahydrodecaborate).

A further advantage of the process according to the invention lies in the fact that the procedure does not require any particular precaution; it can be carried out in an oxidising or non-oxidising atmosphere.

A third advantage of the process according to the invention lies in the use at ordinary temperature of a liquid acid, which is more convenient to handle than hydrochloric acid.

Finally, the yield of bis(alkyl sulphide)-decaborane is considerably higher than that obtained in the second process of the prior art.

The invention relates to a process for the preparation of a bis(alkyl sulphide)-decaborane (12), hereafter called BASD, of the general formula $B_{10}H_{12}(R_2S)_2$, in which R represents a lower alkyl radical, characterised in that a decahydrodecaborate (2−) salt of the general formula $M_2B_{10}H_{10}$, in which M represents a positive radical, is treated with a mixture comprising a strong oxygen-containing acid and an alkyl sulphide of the formula $R_2S$, where R has the above meaning, at a temperature of between −10° C. and 90° C.

The reaction equation can be written in the form:

$$B_{10}H_{10}{}^{2-} + 2H^+ + 2R_2S \rightarrow B_{10}H_{12}(R_2S)_2 \qquad (3)$$

The main by-product of this reaction is boric acid $B(OH)_3$.

According to a first embodiment of the process according to the invention, the said mixture is a solution of a strong oxygen-containing acid which is saturated with an alkyl sulphide.

According to another embodiment, the said mixture is a solution of an alkyl sulphide which is saturated with a strong oxygen-containing acid.

Different $H_{10}H_{10}{}^{2-}$ salts have made it possible to obtain BASD in good yields. By way of non-limiting examples, there may be mentioned $(Et_4N)_2B_{10}H_{10}$, $(Me_4N)_2B_{10}H_{10}$, $(NH_4)_2B_{10}H_{10}$, $K_2B_{10}H_{10}$ and $Na_2B_{10}H_{10}$.

It should be noted that $(Et_4N)_2B_{10}H_{10}$ is obtained directly by the pyrolysis of $Et_4NBH_4$ and that the other $B_{10}H_{10}{}^{2-}$ salts are prepared from $(Et_4N)_2B_{10}H_{10}$ in the conventional way by ion exchange on a cationic resin.

Numerous strong oxygen-containing acids have been used in the synthesis of BASD. By way of example, there may be mentioned sulphuric acid $H_2SO_4$, orthophosphoric acid $H_3PO_4$, perchloric acid ($HClO_4$ (70% strength solution) and fluorosulphonic acid $HFSO_3$.

The yields are greatest when $H_2SO_4$ or $H_3PO_4$ (commercial 85% strength solution to which phosphorus pentoxide $P_2O_5$ is added in order to concentrate it) is employed. The yields of BASD are lower with $HClO_4$ (commercial 70% strength solution) and $HFSO_3$; on the other hand, the amount of boric acid, which is a by-product of the reaction, is significant.

Advantageously, it is appropriate to use an acid which is practically free from water. In fact, BASD is obtained in good yields with 98% strength and 95% strength solutions of sulphuric acid; on the other hand, with 85% strength sulphuric acid, significant amounts of boric acid and only traces of BASD are obtained. Similarly, a fairly low yield is obtained when $HClO_4$ (commercial 70% strength solution) is employed. This can be explained by the presence of significant amounts of water in the acid solution.

The reaction for the synthesis of BASD occurs when lower alkyl sulphides are used as Lewis bases. By way of non-limiting examples, there may be mentioned methyl sulphide ($Me_2S$), ethyl sulphide ($Et_2S$), butyl sulphide ($Bu_2S$) and octyl sulphide ($Oct_2S$).

The best results have been obtained with $Et_2S$. In the case of $Me_2S$, the yield of $B_{10}H_{12}(Me_2S)_2$ is low.

Moreover, it has not been possible to synthesise by this method the BASD derivatives of Lewis bases such as propionitrile $CH_3CH_2CN$ and triethylamine $Et_3N$.

Various tests have been carried out at temperatures of between −10° C. and +90° C. Tests carried out at +60° C. have led to good results which are comparable to those obtained at +20° C. When the reaction is carried out at +90° C., BASD is obtained in very low yield and the formation of $B(OH)_3$ is clearly favoured. On the other hand, at low temperature (−10° C.), a substantial lowering in the yield of BASD is observed. Advantageously, it is appropriate to carry out the reaction at about ambient temperature.

Finally, the reaction time influences the yields. Tests have been carried out, the duration of which was 5, 10 and 90 minutes. It was observed that the BASD, which formed rapidly, was slowly attacked by the excess acid to give boric acid. Advantageously, it is therefore appropriate to carry out the reaction as rapidly as possible.

During the reaction for the synthesis of BASD, the acid is used in excess relative to the amount of $B_{10}H_{10}^{2-}$ salt (about 3 to 4 times the stoichiometic amount). This is explained by the fact that an amount of acid is necessary which is sufficient to allow good contact between the solution and the $B_{10}H_{10}^{2-}$ salt. However, too large an excess of acid (for example, 20 times the stoichiometric amount) favours the formation of boric acid.

In the case where $(Et_4N)_2B_{10}H_{10}$ is used as the decahydrodecaborate (2−) salt, the fact that the former contains $(Et_4N)_2B_{12}H_{12}$ (which is a by-product resulting from the pyrolysis of $Et_4NBH_4$) does not alter the results of the reaction. On the other hand, the presence of $Et_3NBH_3$ (which is another by-product resulting from the pyrolysis of $Et_4NBH_4$) or of the borohydride $Et_4NBH_4$ (which is a residue from the preparation of $(Et_4N)_2B_{10}H_{10}$) involves the formation of considerable amounts of boric acid. Consequently, the product resulting from the pyrolysis of $Et_4NBH_4$ will have to be treated with a mixture of methanol and ether, in which $Et_3NBH_3$ and $Et_4NBH_4$ are soluble.

In the case where any $B_{10}H_{10}^{2-}$ salt is used, the simultaneous presence of the corresponding $B_{12}H_{12}^{2-}$ salt does not alter the results.

In the present process for the preparation of BASD, the alkyl sulphide acts not only as the reactant but also as the extraction solvent. The latter is easily recoverable at the end of the reaction. It has been noted that an alkyl sulphide such as $Me_2S$, $Et_2S$ or $Bu_2S$, and sulphuric acid are, in particular, not miscible in all proportions. Solutions of $R_2S$ dissolved in $H_2SO_4$, which have a composition of about 50/50 (by volume), can be obtained.

The first method of operating the process according to the invention is carried out in the following manner.

The $B_{10}H_{10}^{2-}$ salt is suspended in the sulphide $R_2S$, and the necessary amount of the solution of $R_2S$ dissolved in the strong acid is then added to this suspension; this mixture separates into two phases: the limpid upper phase is a solution of BASD in the sulphide, and the viscous, turbid lower phase contains especially the strong acid and the salt resulting from the reaction. This makes it possible to separate the BASD easily from the reactants and from the reaction products. Several extractions with $R_2S$ are necessary in order to recover the maximum amount of product. It should be noted that the amount of $R_2S$ used during the extractions does not influence the results of the reaction.

After extraction, the BASD is purified in the following manner: the traces of strong acid contained in the organic phase are removed by washing this phase with several portions of an aqueous solution (about 0.1 N) of a weak base (for example $NaHCO_3$), and then with several portions of distilled water. After the solution of $R_2S$ has been dried, for example, over $CaCl_2$, the $R_2S$ is removed by evaporation. The residue is then dissolved in toluene. The solution is filtered, which makes it possible to remove a large part of the boric acid. Hexane is added to the filtrate in order to precipitate $B_{10}H_{12}(R_2S)_2$.

If the alkyl sulphide is soluble in the oxygen-containing acid in all proportions, the BASD cannot be extracted as above. It is necessary to slightly alter the method of operation.

With regard to the second method of operating the process, most of the means described above can be applied to the preparation of the BASD, in which the $B_{10}H_{10}^{2-}$ salt reacts with a solution of a strong acid dissolved in an alkyl sulphide. However, the method of operation is appreciably different. In fact, as the acid is only slightly soluble in the sulphide, it is necessary in this case, in order to obtain a complete attack of the $B_{10}H_{10}^{2-}$ salt, to treat the salt several times in succession with the solution of acid dissolved in the alkyl sulphide.

Other characteristics and advantages of the invention will be better understood on reading the description, which follows, of several embodiments which are given by way of indication and without implying a limitation.

EXAMPLE I

Preparation of $B_{10}H_{12}(Et_2S)_2$ by the action of a solution of $Et_2S$ dissolved in 95% strength $H_2SO_4$ on $(Et_4N)_2B_{10}H_{10}$ (a) Preparation of the solution of $Et_2S$ dissolved in $H_2SO_4$ 20 cm³ of pure $Et_2S$ and 10 cm³ of a 95% strength solution of $H_2SO_4$ are introduced into a 50 cm³ Erlenmeyer flask. This mixture is then stirred in order to bring the temperature back to about ordinary temperature. The mixture is allowed to stand and it is found that two phases form; the upper phase is an organic phase containing $Et_2S$ with traces of sulphuric acid, and the lower phase is a solution of $Et_2S$ dissolved in $H_2SO_4$ (a 50/50 mixture by volume).

(b) Preparation of $B_{10}H_{12}(Et_2S)_2$ 20 ml of pure $Et_2S$ and 0.8 g of pure $(Et_4N)_2B_{10}H_{10}$, that is to say $2.11 \times 10^{-3}$ mol, are introduced into a 50 ml Erlenmeyer flask. 2 ml of the previously prepared solution of $Et_2S$ dissolved in $H_2SO_4$ are then added. Four times the stoichiometric amount of acid necessary according to Reaction 3 are therefore used.

The mixture, which separates into two phases, is stirred for 5 minutes at 20° C. The mixture is allowed to separate out and the upper phase, which consists especially of $Et_2S$ and $B_{10}H_{12}(Et_2S)_2$, is collected. The lower phase (namely the sulphuric phase) is again treated with 20 ml of pure $Et_2S$, by operating as above in order to extract $B_{10}H_{12}(Et_2S)_2$. The operation is repeated 4 times.

The different organic phases are then combined. The resulting solution, which has previously been allowed to stand, is then washed with several portions of a decinormal aqueous solution of $NaHCO_3$, in order to neutralise the $H_2SO_4$ which is dissolved in the $Et_2S$. The organic phase is again washed, but this time with several portions of distilled water, until the pH of the aqueous phase is equal to 7.

The organic phase thus obtained is then dried over $CaCl_2$. The solution is filtered and $Et_2S$ is removed by evaporation in vacuo at 20° C. A yellow viscous residue is obtained which is dissolved in the minimum amount of toluene, in order to remove a large part of the boric acid which is sparingly soluble in this solvent. $B_{10}H_{12}(Et_2S)_2$ is then obtained by precipitation on adding hexane to the toluene solution. $B_{10}H_{12}(Et_2S)_2$ is then washed with hexane and dried in vacuo at 20° C.

0.43 g of $B_{10}H_{12}(Et_2S)_2$ (yield 68%) is obtained and is identified by its infrared and NMR spectra and by the fact that it reacts with $Et_3N$ to form $B_{10}H_{12}(Et_3N)_2$ and $(Et_3NH)_2B_{10}H_{10}$.

EXAMPLE II

Preparation of $B_{10}H_{12}(Et_2S)_2$ by the action of a solution of $Et_2S$ dissolved in $H_3PO_4$ on $(Et_4N)_2B_{10}H_{10}$ (a) Preparation of the solution of $Et_2S$ dissolved in $H_3PO_4$ 20 cm³ of pure $Et_2S$ and 10 cm³ of a commercial 85% strength solution of $H_3PO_4$, to which $P_2O_5$ is previously added, are introduced into a 50 cm³ Erlenmeyer flask. The reaction is carried out as in Example I a), and the lower phase, which forms after separation, is a solution of $Et_2S$ dissolved in $H_3PO_4$.

(b) Preparation of $B_{10}H_{12}(Et_2S)_2$ 10 ml of pure $Et_2S$ are introduced into a 50 cm³ Erlenmeyer flask together with 0.3 g of a product resulting from the pyrolysis of $Et_4NBH_4$ and containing 87.5% by weight of $(Et_4N)_2B_{10}H_{10}$, that is to say $0.65 \times 10^{-3}$ mol, and 12.5% of $(Et_4N)_2B_{12}H_{12}$ which is very difficult to remove. 2 ml of the previously prepared solution of $Et_2S$ dissolved in $H_3PO_4$ are then added.

The mixture separates into two phases and is stirred for 5 minutes at 20° C. It is allowed to separate and the upper phase, which consists especially of $Et_2S$, $B_{10}H_{12}(Et_2S)_2$ and small amounts of $H_3PO_4$, is collected. The lower phase ($H_3PO_4$) is treated with 10 ml of pure $Et_2S$ and the new upper phase which forms is collected as above.

This operation is repeated four times.

The different organic phases are then combined. The separation and purification of $B_{10}H_{12}(Et_2S)_2$ are carried out as in Example I (b).

0.108 g of $B_{10}H_{12}(Et_2S)_2$ is collected, which corresponds to a yield of 52%. $B_{10}H_{12}(Et_2S)_2$ is identified by its infrared and NMR spectra.

EXAMPLE III

Preparation of $B_{10}H_{12}(Oct_2S)_2$ by the action of a solution of octyl sulphide dissolved in a 98% strength solution of $H_2SO_4$ on $(Et_4N)_2B_{10}H_{10}$ (a) Preparation of the solution of octyl sulphide dissolved in 98% strength $H_2SO_4$ As the octyl sulphide is soluble in sulphuric acid in all proportions, only one phase is formed.

A sulphide-acid mixture in the proportions 75/25 by volume is therefore prepared directly.

(b) Preparation of $B_{10}H_{12}(Oct_2S)_2$ 10 ml of octyl sulphide and 0.28 g of $(Et_4N)_2B_{10}H_{10}$ are introduced into a 50 ml Erlenmeyer flask. 2 ml of the previously prepared solution of octyl sulphide dissolved in $H_2SO_4$ are then added.

Only one phase is formed. The reaction mixture is stirred for 15 minutes at 20° C. The solution is filtered in order to remove the solid particles. The solution is washed with several portions of a decinormal solution of $NaHCO_3$, which makes it possible to neutralise the sulphuric acid. The organic phase is then washed with several portions of distilled water until the pH of the aqueous phase is equal to 7. The organic phase containing the octyl sulphide and the bis(octyl sulphide)-decaborane is dried over $CaCl_2$. The solution is filtered and the filtrate is collected.

$B_{10}H_{12}(Oct_2S)_2$ is identified in solution in octyl sulphide by its infrared and NMR spectra.

EXAMPLE IV

Preparation of $B_{10}H_{12}(Et_2S)_2$ by the action of a solution of $Et_2S$ dissolved in 98% strength $H_2SO_4$ on $K_2B_{10}H_{10}$ (a) Preparation of the solution of $Et_2S$ dissolved in 98% strength $H_2SO_4$ This is identical to the preparation in Example I (a).

(b) Preparation of $B_{10}H_{10}(Et_2S)_2$ 10 ml of pure $Et_2S$ and 0.3 g of $K_2B_{10}H_{10}$ are introduced into a 50 ml Erlenmeyer flask. 1 ml of a solution of $Et_2S$ dissolved in $H_2SO_4$, as prepared previously, is then poured into the flask. The mixture separates into two phases and is stirred for 5 minutes at 20° C.

It is allowed to separate out and the upper phase, which consists especially of $Et_2S$, $B_{10}H_{12}(Et_2S)_2$ and small amounts of $H_2SO_4$, is collected. The lower phase (namely the sulphuric phase) is treated with 10 ml of pure $Et_2S$, and the upper phase is collected as above. This operation is carried out four times.

The different organic phases are then combined; the separation and purification of $B_{10}H_{12}(Et_2S)_2$ are carried out as in Example I (b).

$B_{10}H_{12}(Et_2S)_2$ is identified by its infrared and NMR spectra.

EXAMPLE V

Preparation of $B_{10}H_{12}(Et_2S)_2$ by the action of a solution of $H_2SO_4$ (95% strength) dissolved in $Et_2S$ on $(NH_4)_2B_{10}H_{10}$ 1 g of $(NH_4)_2B_{10}H_{10}$ ($6.5 \times 10^{-3}$ mol) is introduced into A (see FIG. 1), and 3 cm³ of 95% strength $H_2SO_4$ and 15 cm³ of pure $Et_2S$ are introduced into B. B is cooled to the temperature of liquid air and the apparatus is placed under vacuum. B is then reheated to ambient temperature. The mixture contained in B is then stirred at this temperature for 15 hours in order to bring the solution of $Et_2S$ in $H_2SO_4$ to saturation. It is observed that part of the $Et_2S$ dissolves in the $H_2SO_4$. The mixture is then allowed to separate, and the upper phase, which consists of $Et_2S$ in which $H_2SO_4$ is dissolved, is then poured into A. The reaction mixture thus obtained is stirred for 5 hours. $Et_2S$ is thereafter distilled by cooling B in liquid air and keeping A at ambient temperature. B is then reheated to 20° C. and the above operation, which consists in bringing the solution of $Et_2S$ in $H_2SO_4$ to saturation, is recommended, $(NH_4)_2B_{10}H_{10}$ is again treated with this new solution. $(NH_4)_2B_{10}H_{10}$ undergoes a total of 5 treatments. At the end of the 5th treatment, $Et_2S$ is kept in the reaction medium. The solution contained in A is filtered and the filtrate is collected. This filtrate, which consists of $Et_2S$, $B_{10}H_{12}(Et_2S)_2$ and small amounts of $H_2SO_4$, is washed several times with distilled water, until a pH which is equal to 7 is obtained, in order to remove $H_2SO_4$. The organic phase is recovered and dried over $CaCl_2$. This solution is filtered and the filtrate, which consists of $Et_2S$ and the bis-ligand, is collected. $Et_2S$ is evaporated off in vacuo at 20° C. 0.31 g of $B_{10}H_{12}(Et_2S)_2$ (yield 17%) is obtained and is characterised by its infrared and NMR spectra and by the fact that it reacts with hex-l-yne to form n-butylcarborane. It should be carefully noted, that prior art process described in U.S. Pat. No.

3,489,812 cannot be applied to other $B_{10}H_{10}^{-2-}$ salts than $(NH_4)_2B_{10}H_{10}$. It should be appreciated that $(Et_4N)_2B_{10}H_{10}$ is a very valuable starting material compared to $(NH_4)_2B_{10}H_{10}$, since $(Et_4N)_2B_{10}H_{10}$ can be easily obtained from $Et_4N\ BH_4$ by pyrolysis and since $Et_4NBH_4$ can itself be easily obtained by ion exchange from $KBH_4$ according to the process described in U.S. Ser. No. 695,825, filed June 14, 1976, now abandoned. On the contrary $(NH_4)_2B_{10}H_{10}$ cannot be prepared so advantageously because $NH_4BH_4$ is unstable. Further the preparation of $(NH_4)_2B_{10}H_{10}$ from $(Et_4N)_2B_{10}H_{10}$ is tedious because it necessitates, by principle, the solubilization of all the $(Et_4N)_2B_{10}H_{10}$ in water which finally implies the handling and the removing of a great amount of water per mole of $(NH_4)_2B_{10}H_{10}$ because the solubility of $(Et_4N)_2B_{10}H_{10}$ in water is weak (about 5g/liter at usual ion exchange temperature).

What is claimed is:

1. A process for the preparation of bis(alkyl sulphide) decaborane (12) of formula $B_{10}H_{12}(R_2S)_2$ in which R is lower alkyl which comprises reacting a decahydrododecaborate (2−) salt of formula $(NR'_4)_2B_{10}H_{10}$ wherein R' is methyl or ethyl with a mixture consisting of a strong oxygen-containing acid and an alkyl sulphide of formula $R_2S$, wherein R is said lower alkyl at a temperature of between $-10°$ C. and $90°$ C.

2. Process according to claim 1, wherein R is chosen from the group: methyl, ethyl, butyl and octyl.

3. Process according to claim 1, wherein the oxygen-containing acid is chosen from the group: $H_2SO_4$, $H_3PO_4$, $HFSO_3$ and $HClO_4$.

4. Process according to claim 1, wherein the said mixture is a solution of a strong oxygen-containing acid which is saturated with an alkyl sulphide.

5. Process according to claim 4, wherein R is ethyl M is tetraethylammonium and the strong oxygen-containing acid is sulphuric acid of at least 90% strength.

6. Process according to claim 4, wherein R is ethyl M is tetraethylammonium radical, and the strong oxygen-containing acid is orthophosphoric acid to which phosphorus pentoxide is added.

7. Process according to claim 4, wherein R is octyl M is tetraethylammonium rdical, and the oxygen-containing acid is sulphuric acid of at least 95% strength.

8. Process according to claim 1, wherein the temperature is about 20° C. and the reaction time is about 5 minutes.

9. Process according to claim 1, wherein the said mixture is a solution of an alkyl sulphide which is saturated with a strong oxygen-containing acid.

* * * * *